US008591907B2

(12) United States Patent
Mistrello et al.

(10) Patent No.: US 8,591,907 B2
(45) Date of Patent: Nov. 26, 2013

(54) **HYPOALLERGENIC VARIANTS OF THE MAJOR ALLERGEN FROM *BETULA VERRUCOSA* POLLEN**

(75) Inventors: Giovanni Mistrello, Milan (IT); Stefania Zanotta, Milan (IT); Daniela Roncarolo, Milan (IT); Paolo Falagiani, Milan (IT)

(73) Assignee: Lofarma S.p.A., Milan (IT)

( * ) Notice: Subject to any disclaimer, the term of this patent is extended or adjusted under 35 U.S.C. 154(b) by 430 days.

(21) Appl. No.: 12/679,207

(22) PCT Filed: Sep. 16, 2008

(86) PCT No.: PCT/EP2008/007726
§ 371 (c)(1),
(2), (4) Date: May 20, 2010

(87) PCT Pub. No.: WO2009/036949
PCT Pub. Date: Mar. 26, 2009

(65) Prior Publication Data

US 2010/0310590 A1 Dec. 9, 2010

(30) Foreign Application Priority Data

Sep. 19, 2007 (IT) .............................. MI2007A1819

(51) Int. Cl.

| | |
|---|---|
| ***A61K 38/00*** | (2006.01) |
| ***A61K 38/04*** | (2006.01) |
| ***A61K 39/00*** | (2006.01) |
| ***C07K 2/00*** | (2006.01) |
| ***C07K 4/00*** | (2006.01) |
| ***C07K 5/00*** | (2006.01) |
| ***C07K 7/00*** | (2006.01) |
| ***C07K 14/00*** | (2006.01) |
| ***C07K 16/00*** | (2006.01) |
| ***C07K 17/00*** | (2006.01) |

(52) U.S. Cl.
USPC ......... 424/185.1; 530/300; 530/324; 530/326

(58) Field of Classification Search
None
See application file for complete search history.

(56) References Cited

FOREIGN PATENT DOCUMENTS

WO WO 2007/073907 A1 7/2007

OTHER PUBLICATIONS

Xiang et al. 'C-Terminal 23 kDa polypeptide of soybean Gly m Bd 28 K is a potential allergen.' Planta 220:56-63, 2004.*

Ngo et, al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*

Blumenthal et al. 'Definition of an Allergen.' Allergens and Allergen Immunotherapy. Ed. R Lockey, S. Bukantz and J. Bousquet. New York: Marcel Decker, 2004. 37-50.*

Skolnick et al. 'From genes to protein structure and function: novel applications of computational approaches in the genomic era.' Trends in Biotech. 18:34-39, 2000.*

Attwood et al. 'The Babel of Bioinformatics.' Science. 290(5491):471-473, 2000.*

Kuby et al. 'Immunology.' Fourth Edition, Chapter 18: 449-465, 2000.*

Vrtala Susanne et al.; "High-level expression in *Escherichia coli* and purification of recombinant plant profilins: Comparison of IgE-binding capacity and allergenic activity"; Biochemical and Biophysical Research Communications; vol. 226; No. 1; 1996; pp. 42-50; XP002506727; ISSN: 0006-291X.

Federov Alexander A. et al.; "The molecular basis for allergen cross-reactivity : Crystal structure and IgE-epitope mapping of birch pollen profilin"; Structure (London); vol. 5; No. 1; 1997; pp. 33-45; XP002506728; ISSN: 0969-2126.

Radauer C. et al.; "Cross-reactive and species-specific immunoglobulin E epitopes of plant profilins: an experimental and structure-based analysis"; Clinical and Experimental Allergy; vol. 36; No. 7; Jul. 2006; pp. 920-929; XP002506729; ISSN: 0954-7894.

* cited by examiner

*Primary Examiner* — Nora Rooney
(74) *Attorney, Agent, or Firm* — Arent Fox LLP

(57) ABSTRACT

The invention provides hypoallergenic variants of Bet v 2 major allergen from *Betula verrucosa* plant pollen and the use thereof for the preventive or therapeutic treatment of allergic diseases.

8 Claims, 4 Drawing Sheets

SEQUENCE LISTING

```
<160> NUMBER OF SEQ ID NOS: 15

<210> SEQ ID NO 1
<211> LENGTH: 133
<212> TYPE: PRT
<213> ORGANISM: Betula verrucosa
<220> FEATURE:
<223> OTHER INFORMATION: Bet v 2 wt from Betula verrucosa

<400> SEQUENCE: 1

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95
```

```
Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130


<210> SEQ ID NO 2
<211> LENGTH: 133
<212> TYPE: PRT
<213> ORGANISM: Betula verrucosa
<220> FEATURE:
<223> OTHER INFORMATION: Bet v 2 mutant

<400> SEQUENCE: 2

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ala Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130


<210> SEQ ID NO 3
<211> LENGTH: 133
<212> TYPE: PRT
<213> ORGANISM: Betula verrucosa
<220> FEATURE:
<223> OTHER INFORMATION: Bet v 2 mutant

<400> SEQUENCE: 3

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Thr Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125
```

```
Ile Asp Gln Gly Leu
    130


<210> SEQ ID NO 4
<211> LENGTH: 133
<212> TYPE: PRT
<213> ORGANISM: Betula verrucosa
<220> FEATURE:
<223> OTHER INFORMATION: Bet v 2 mutant

<400> SEQUENCE: 4

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Gly Glu Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130


<210> SEQ ID NO 5
<211> LENGTH: 133
<212> TYPE: PRT
<213> ORGANISM: Betula verrucosa
<220> FEATURE:
<223> OTHER INFORMATION: Bet v 2 mutant

<400> SEQUENCE: 5

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Lys Ser Phe Pro Gln Phe Thr Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Gly Glu Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130


<210> SEQ ID NO 6
<211> LENGTH: 133
```

```
<212> TYPE: PRT
<213> ORGANISM: Betula verrucosa
<220> FEATURE:
<223> OTHER INFORMATION: Bet v 2 mutant

<400> SEQUENCE: 6

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ala Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Gly Glu Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130


<210> SEQ ID NO 7
<211> LENGTH: 402
<212> TYPE: DNA
<213> ORGANISM: Betula verrucosa
<220> FEATURE:
<223> OTHER INFORMATION: sequence encoding Bet v 2 wt from Betula
      verrucosa

<400> SEQUENCE: 7

atgtcgtggc aaacgtacgt ggatgaacat ttgatgtgcg atatcgacgg gcaagccagc      60

aactcgctgg catctgcgat cgtcggtcac gatggctctg tgtgggccca gagctcttcc     120

ttcccacagt ttaagcctca ggaaatcact ggtatcatga aggactttga ggagccgggt     180

catcttgctc cgacgggctt acaccttggg ggcataaaat acatggtcat ccagggagag     240

gctggtgctg tcatccgtgg aaagaaggga tctggaggta ttactataaa gaagactggt     300

caagctctcg tttttggcat ctatgaagag cctgtgacac caggacagtg caacatggtt     360

gttgagaggt tgggggatta ccttattgac cagggcctgt ag                        402


<210> SEQ ID NO 8
<211> LENGTH: 402
<212> TYPE: DNA
<213> ORGANISM: Betula verrucosa
<220> FEATURE:
<223> OTHER INFORMATION: sequence encoding a Bet v 2 mutant

<400> SEQUENCE: 8

atgtcgtggc aaacgtacgt ggatgaacat ttgatgtgcg atatcgacgg gcaagccagc      60

aactcgctgg catctgcgat cgtcggtcac gatggctctg tgtgggccca gagcgcttcc     120

ttcccacagt ttaagcctca ggaaatcact ggtatcatga aggactttga ggagccgggt     180

catcttgctc cgacgggctt acaccttggg ggcataaaat acatggtcat ccagggagag     240

gctggtgctg tcatccgtgg aaagaaggga tctggaggta ttactataaa gaagactggt     300

caagctctcg tttttggcat ctatgaagag cctgtgacac caggacagtg caacatggtt     360
```

-continued gttgagaggt tgggggatta ccttattgac cagggcctgt ag 402

<210> SEQ ID NO 9
<211> LENGTH: 402
<212> TYPE: DNA
<213> ORGANISM: Betula verrucosa
<220> FEATURE:
<223> OTHER INFORMATION: sequence encoding a Bet v 2 mutant

<400> SEQUENCE: 9
atgtcgtggc aaacgtacgt ggatgaacat ttgatgtgcg atatcgacgg gcaagccagc 60
aactcgctgg catctgcgat cgtcggtcac gatggctctg tgtgggccca gagctcttcc 120
ttcccacagt ttacgcctca ggaaatcact ggtatcatga aggactttga ggagccgggt 180
catcttgctc cgacgggctt acaccttggg ggcataaaat acatggtcat ccagggagag 240
gctggtgctg tcatccgtgg aaagaaggga tctggaggta ttactataaa gaagactggt 300
caagctctcg tttttggcat ctatgaagag cctgtgacac caggacagtg caacatggtt 360
gttgagaggt tgggggatta ccttattgac cagggcctgt ag 402

<210> SEQ ID NO 10
<211> LENGTH: 402
<212> TYPE: DNA
<213> ORGANISM: Betula verrucosa
<220> FEATURE:
<223> OTHER INFORMATION: sequence encoding a Bet v 2 mutant

<400> SEQUENCE: 10
atgtcgtggc aaacgtacgt ggatgaacat ttgatgtgcg atatcgacgg gcaagccagc 60
aactcgctgg catctgcgat cgtcggtcac gatggctctg tgtgggccca gagctcttcc 120
ttcccacagt ttaagcctca ggaaatcact ggtatcatga aggactttga ggagccgggt 180
catcttgctc cgacgggctt acaccttggg ggcataaaat acatggtcat ccagggagag 240
gctggtgctg tcatccgtgg aggggaggga tctggaggta ttactataaa gaagactggt 300
caagctctcg tttttggcat ctatgaagag cctgtgacac caggacagtg caacatggtt 360
gttgagaggt tgggggatta ccttattgac cagggcctgt ag 402

<210> SEQ ID NO 11
<211> LENGTH: 402
<212> TYPE: DNA
<213> ORGANISM: Betula verrucosa
<220> FEATURE:
<223> OTHER INFORMATION: sequence encoding a Bet v 2 mutant

<400> SEQUENCE: 11
atgtcgtggc aaacgtacgt ggatgaacat ttgatgtgcg atatcgacgg gcaagccagc 60
aactcgctgg catctgcgat cgtcggtcac gatggctctg tgtgggccca gagctcttcc 120
ttcccacagt ttacgcctca ggaaatcact ggtatcatga aggactttga ggagccgggt 180
catcttgctc cgacgggctt acaccttggg ggcataaaat acatggtcat ccagggagag 240
gctggtgctg tcatccgtgg aggggaggga tctggaggta ttactataaa gaagactggt 300
caagctctcg tttttggcat ctatgaagag cctgtgacac caggacagtg caacatggtt 360
gttgagaggt tgggggatta ccttattgac cagggcctgt ag 402

<210> SEQ ID NO 12
<211> LENGTH: 402
<212> TYPE: DNA
<213> ORGANISM: Betula verrucosa -continued

```
<220> FEATURE:
<223> OTHER INFORMATION: sequence encoding a Bet v 2 mutant

<400> SEQUENCE: 12

atgtcgtggc aaacgtacgt ggatgaacat ttgatgtgcg atatcgacgg gcaagccagc     60

aactcgctgg catctgcgat cgtcggtcac gatggctctg tgtgggccca gagcgcttcc    120

ttcccacagt ttaagcctca ggaaatcact ggtatcatga aggactttga ggagccgggt    180

catcttgctc cgacgggctt acaccttggg ggcataaaat acatggtcat ccagggagag    240

gctggtgctg tcatccgtgg aggggaggga tctggaggta ttactataaa gaagactggt    300

caagctctcg tttttggcat ctatgaagag cctgtgacac caggacagtg caacatggtt    360

gttgagaggt tgggggatta ccttattgac cagggcctgt ag                       402


<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

gggcccagag cgcttccttc ccacag                                          26


<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

ccttcccaca gtttacgcct caggaaatc                                       29


<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

gtcatccgtg gaggggaggg atctggag                                        28
```

HYPOALLERGENIC VARIANTS OF THE MAJOR ALLERGEN FROM *BETULA VERRUCOSA* POLLEN

CROSS-REFERENCE TO RELATED APPLICATION

Figure 1:
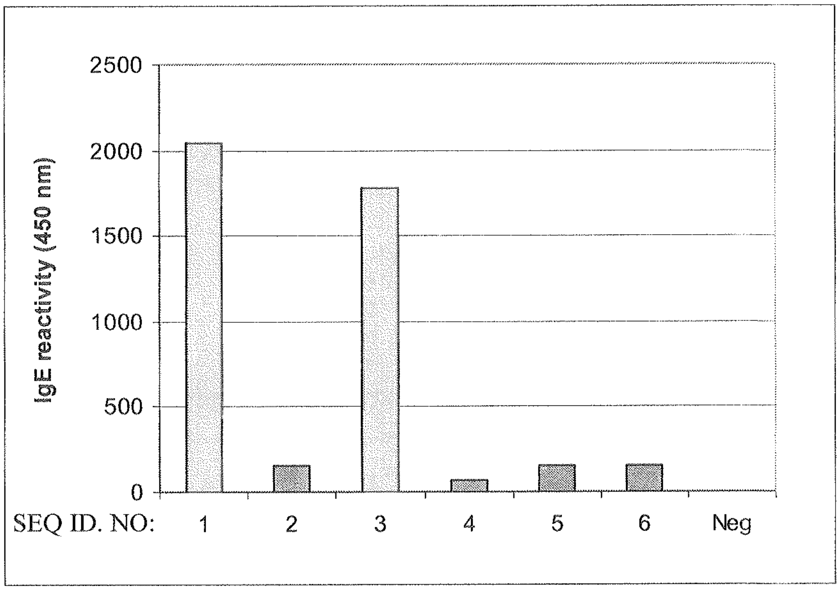

This application is a National Stage entry of International Application No. PCT/EP2008/007726, filed Sep. 16, 2008, which claims priority to Italian Patent Application No. M12007A001819, filed Sep. 19, 2007. The disclosure of the prior application is hereby incorporated in its entirety by reference.

SEQUENCE LISTING

The instant application contains a Sequence Listing which has been submitted in ASCII format via EFS-Web and is hereby incorporated by reference in its entirety. Said ASCII copy, created on Oct. 19, 2012, is named 10050600.txt and is 12,549 bytes in size.

The present invention provides hypoallergenic sequence variants of the Bet v 2 protein, nucleic acid molecules encoding them, pharmaceutical compositions containing the same and their use in the prophylaxis and therapy of allergic diseases caused by pollen of plants from *Betula verrucosa* species.

BACKGROUND OF THE INVENTION

Allergies are caused by a dysfunction in the immune system, which reacts to innocuous proteins contained in pollen, mites, epithelia and certain foods by producing IgE-class antibodies.

Recent data indicate that above 10% of the population in Western countries suffer from this disease, the symptoms of which may deteriorate with time giving rise to e.g. asthma or a sensitization to other allergens thus making more difficult the choice of the appropriate therapy.

Specific hyposensitizing immunotherapy (SIT), unlike pharmacological therapy, is the only etiological treatment of allergic diseases capable of favourably changing the immunological parameters characteristic of such diseases.

The hyposensitizing immunotherapy consists in the administration of increasing doses of standardized extracts (vaccines) obtained from the same substance which causes the disease (1). In this way, a sort of immunological tolerance to said substance is gradually induced in the patient with following disappearance of the allergic symptoms.

However, the risk of eliciting serious side effects (2), although remarkably reduced with the use of either slow-release vaccines or vaccines administered through routes alternative to injection, has in fact limited the application of specific hyposensitizing immunotherapy in the treatment of allergic diseases.

In recent years, most attention has been focused on the development of effective, safer vaccines, particularly vaccines consisting of mutagenized recombinant proteins, i.e. hypoallergenic variants capable of favourably influencing the natural progression of the disease without causing undesired side effects (3).

One of the beneficial factors of SIT is the induction if IgG antibodies specific for the sensitizing allergen. These (protective) antibodies can inhibit the antigen-IgE binding, specifically the IgE binding to Bet v 2 antigen, altering the molecule's tridimensional conformation (4,5). The development of vaccines containing hypoallergenic recombinant proteins with unaltered immunogenic properties may improve the therapeutic approach to allergic diseases.

The pollen of plants taxonomically known as Fagales (birch, alder, hazel, oak, hornbeam) is one of the most important causes of allergic rhinitis and asthma in the temperate regions. The two major allergens of birch pollen. Bet v 1 (cDNA deposited at GenBank acc. No. X15877) and Bet v 2 (acc. No. M65179) are proteins with molecular weight of 17 and 14 kD, respectively (6, 7). Bet v 2 belongs to the profilin family, which are ubiquitous cytoplasmic proteins involved in the regulation of eukaryotic cell cytoskeleton. They specifically interact with at least two cellular (macro)molecules, that is, phosphatidylinositol-4,5-bisphosphate, thereby preventing the hydrolysis of this fatty acid by C-$\gamma$ phospholypase (8), and actin, modulating its polymerization (9). The high expression of profilins in mature and germinative pollen suggests their involvement in the regulation of the microfilament precursors which take part in the germination process (10). Profilins were identified as allergens in the pollen from many arboreous and herbaceous plants and in many fruits and vegetables and thus they were defined 'pan-allergens', despite the fact that they are found in only 20% of patients allergic to pollen (11, 12).

The high sequence homology, higher than 60% in most plant profilins of various origin, causes cross-sensitization not only with pollen from botanically correlated (13) and non-correlated (14) plants but also between pollen and plant aliments (15) or between pollen and latex (16). The homology between plant and mammalian profilins is rather low, nonetheless they proved able to bind actin from different species and showed interchangeability (17, 18, 19). An explanation is that all profilins share a similar tridimensional structure, as shown using X-ray crystallography (20, 21, 22).

Many studies confirm the immunologic equivalence of profilins. In fact it was shown that IgEs from patients sensitized to a determined profilin are able to bind profilins of different origin and that IgE binding to profilins can be mutually inhibited (16).

The high cross-reactivity between different profilins allows the use of a single profilin for allergy diagnosis and recombinant Bet v 2 is often used as the allergen of choice for profilin-specific IgE determination (23, 24).

There are many studies on the determination of profilin IgE epitopes.

Vrtala (1996) (25) mutagenized Bet v 2 at positions Phe44 and Gln47, which were changed in Tyr44, Glu47 and Asn47, according to contemporaneous studies carried out by the some group (26), where a linear epitope recognized by the monoclonal antibody 4A6 was identified. The epitope recognized by this antibody was mapped using synthetic dodecapeptides which spanned the entire amino acid sequence of Bet v2. The peptides which more efficiently bound the antibody contained the regions between amino acids 38-49 and 40-51. The importance of Gln47 residue in the IgG-peptide binding was supported by the evidence that 4A6 was not able to recognize the profilins from *Nicotiana tabacum* and *Phleum pratense*, whose sequences present a glutamate in place of Gln47 in Bet v 2. Unlike the Gln47→Glu47 mutation, the change from Phe44 to Tyr44 or from Gln47 to Asn47 did not affect the antibody binding. The same mutations (Gln47 to Glu or Asn and Phe44 to Tyr44) applied to recombinant Bet v 2 were unable to diminish the binding between profilin and IgE, as shown by immunoblotting and ELISA experiments (25).

In a subsequent study published in 1997 (22), the main IgE epitopes were identified by cloning random fragments of birch profilin cDNA from an expression library assayed with sera from patients allergic to profilins. Three regions, corresponding to the alpha helices located at the amino (aa 1-30) and carboxy (aa 106-132) termini and to a fragment comprised between residues 30 and 50, proved more reactive.

In a subsequent study (23), the search for IgE epitopes was based on the comparison between theoretical structural models for profilins from different plants and birch or latex profilin crystals. Eleven potential conformational epitopes were predicted, consisting of contiguous amino acid regions, at least 20% of which are surface-exposed. Two types of epitopes resulted from a comparison of the amino acid sequences with the conformational models: the species-specific ones, characterised by a high variability, and the highly conserved ones, which are more likely involved in the cross-reactivity between profilins from different plants. The amino acid sequence alignments reflect the results of Fedorov's study (22), evidencing two potential linear epitopes at the N-terminus, three in the region between residues 30 and 80 and additional two at the profilin C-terminus. All these regions are highly conserved in the plant profilins assessed in this study. The prediction of potential conformational epitopes was based on the analysis of a 3D model for the latex profilin Hev b 8. The analysis evidenced 12 protruding residues, selected as centres of the epitopes. Although all potential epitopes were conformational, they contained linear sequences and either conserved or variable residues. No test was reported in this study to confirm the specific IgE-binding capability of the proposed epitopes.

A more recent publication concerns the identification of IgE epitopes of *Cucumis melo's* profilin (27). By determining the IgE reactivity of peptides spanning the entire amino acid sequence of this protein, two linear epitopes were identified, which are strongly recognized by the serum of patients allergic to melon: E1, comprising residues 66-75 and 81-93, and E2 consisting of amino acids 95-99 and 122-131. Two additional epitopes were characterised by a weaker IgE response, namely E3 (residues 2-10) and E4 (35-45). The overlap of peptides corresponding to epitopes E1 and E2 with the melon profilin 3D model, indicates two regions with well-defined electrostatic properties: E1 and E2, which are associated with electropositive and electronegative protein domains, respectively.

The data available from the literature suggest the molecular portions where the IgE profilin epitopes are located but fail to indicate the amino acids involved in IgE binding.

DESCRIPTION OF THE INVENTION

It has now been found that by replacing or deleting one or more amino acid residues within the sequence of the Bet v 2 allergen, this becomes less reactive to the IgE antibodies.

In a first aspect, the invention provides a hypoallergenic protein which is a sequence variant of the Bet v 2 allergen and which is characterized by:

1) reduced reactivity to IgEs compared to wild-type Bet v 2 allergen (SEQ ID NO:1);

2) an amino acid sequence which:

a) is at least 90%, preferably at least 93%, more preferably at least 97% identical to SEQ ID NO:1;

b) in a sequence alignment with SEQ ID NO:1, presents at least one substitution or deletion at the Ser or Lys residues matching $Ser_{39}$, $Lys_{45}$, $Lys_{88}$ or $Lys_{89}$ in SEQ ID NO:1.

In a preferred embodiment, the variants of the Bet v 2 allergen according to the invention present a number of substitutions or deletion varying from 1 to 3 at the indicated positions, whereby single-, double- or triple substitution and/or deletion variants are generated. Although substitutions and deletions of different amino acid residues can be simultaneously present in Bet v 2 molecule, the variants obtained by sole substitution of one or more residues at the indicated positions are preferred, especially those in which such residues are replaced with a neutral, polar or acidic amino acid, which is preferably selected from Ala, Thr, Gly, Pro, Leu, Ile, Ser, Phe, Glu, Asp, more preferably from Ala, Thr, Ser, Gly, Glu, Asp.

Examples of variants according to the invention are identified in SEQ ID NO:2 (1 residue substitution), SEQ ID NO:3 (1 res. subst.), SEQ ID NO:4 (2 res. subst.), SEQ ID NO:5 (3 res. subst.) and SEQ ID NO:6 (3 res. subst.).

Compared to the wild-type counterpart. Bet v 2 allergen substitution and/or deletion variants according to the invention show a IgE reactivity to the serum of *Betula verrucosa* pollen-allergic patients which is reduced by at least 10%, preferably at least 50%, more preferably at least 90%, wherein the IgE reactivity is measured e.g. by means of an ELISA assay.

The IgE reactivity of the proteins SEQ ID NOs:2-6 from a pool of sera of allergic patients was tested in an ELISA assay (FIG. 1). Compared to the wt Bet v 2 allergen (SEQ ID NO:1), a 92% (SEQ ID NO:2), 13% (SEQ ID NO:3), 97% (SEQ ID NO:4) and 93% (SEQ ID NO.s:5 and 6) mean reduction of IgE reactivity was observed when such proteins were incubated with serum pool from patients allergic to birch pollen.

Figure 2:
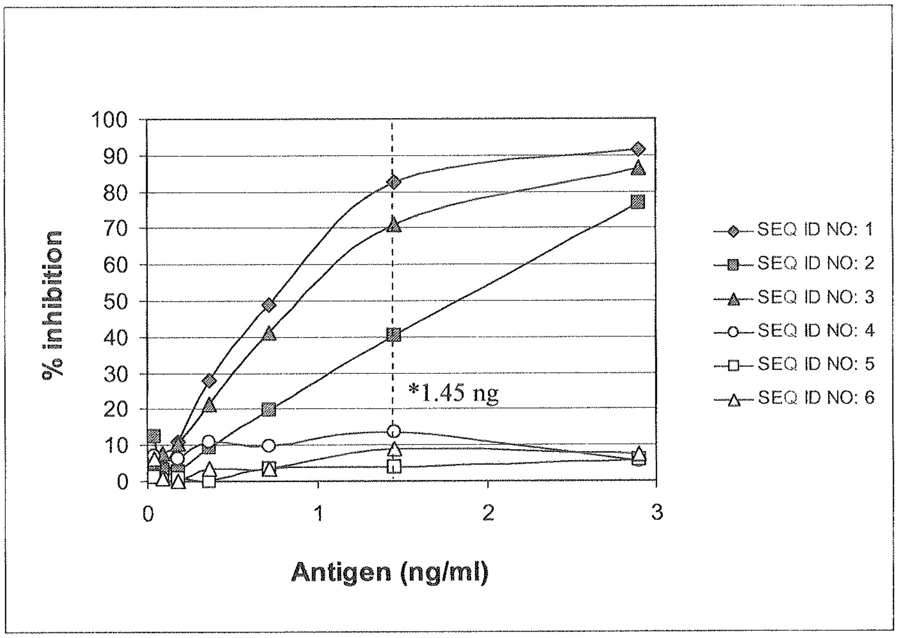

These results were confirmed by experiments of REAST inhibition, which allow to evaluate the reactivity of homologous epitopes from different proteins. In the presence of 1.45 ng of inhibitor, the binding of Bet v 2 wt (SEQ ID NO:1) to IgEs from a serum pool of allergic patients is inhibited by 82.6% when the serum is pre-treated with the same protein, by 40.4% and 71% when the serum is pre-incubated with the variants SEQ ID NO:2 and SEQ ID NO:3, respectively, while the observed inhibition is only 13.4%, 4% and 8.8% when the serum is pre-incubated with identical amounts of respectively the double-substitution variant (SEQ ID NO:4) and triple-substitution variants (SEQ ID NO:5 and SEQ ID NO:6) (FIG. 2).

These results clearly indicate that the amino acids at positions 39, 45, 88, 89 of SEQ ID NO:1 are involved in the recognition of Bet v 2 allergen by IgEs.

Figure 3:
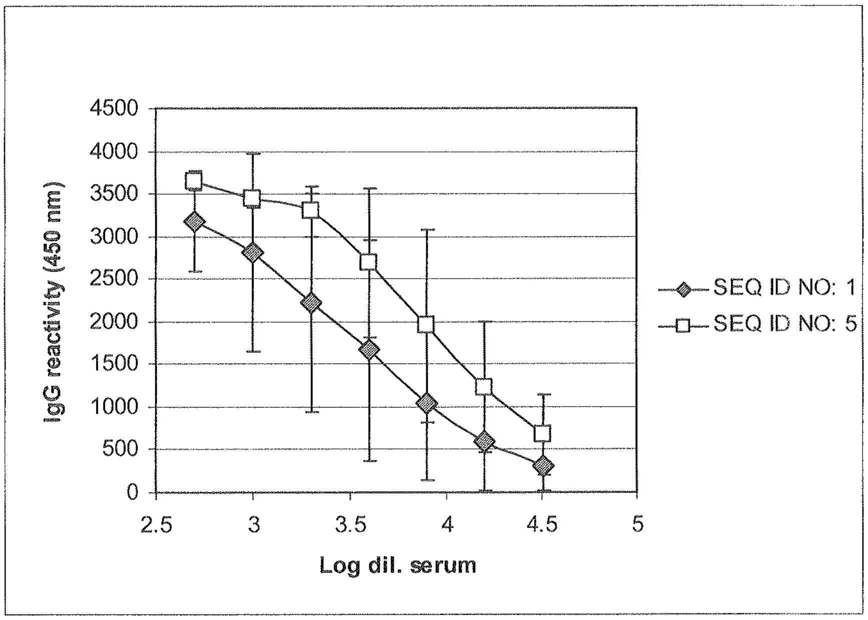

In addition, in experiments of Balb/c mouse immunization, both the Bet v 2 wt allergen and the hypoallergenic protein SEQ ID NO:5 (chosen as an exemplary mutated allergen) proved able to induce a IgG-specific immune response (FIG. 3). The antibodies against SEQ ID NO:5 were able to recognize the wt-counterpart SEQ ID NO:1 (FIG. 4), demonstrating that the replacement of Lys-residues at the positions 45, 88, 89 does not determine a significant alteration of the molecule immunogenicity and of its IgG epitopes. In contrast, the antibodies present in the serum of mice immunized with a non-correlated antigen were not able to recognize either wt Bet v 2 or SEQ ID NO:5.

In a further aspect, the invention provides an immunologically active peptide corresponding to a Bet v 2 fragment containing at least one of the above-described substitutions and/or deletions. Said peptide preferably contains from 15 to 35, more preferably from 15 to 20 amino acid residues. As used herein, the expression "immunologically active peptide" indicates a peptide that is able to elicit a IgE-independent immune response.

The substitution and/or deletion variants according to the invention can be easily prepared by mutagenesis of Bet v 2 wt cDNA sequence (SEQ ID NO:7) using methods and techniques known to those skilled in the art.

The cDNA sequences coding for the single, double and triple substitution variants identified in SEQ ID NOs: 2-6 are reported in SEQ ID NOs: 8-12.

In further aspects the invention provides a nucleic acid molecule encoding a hypoallergenic Bet v 2 variant herein disclosed, or a peptide derived therefrom, and an expression vector containing said molecule functionally linked to genetic elements controlling its expression in eukaryotic or prokaryotic cells, such as transcription promoters, enhancers, signal and leader sequences or other sequences involved in transcription regulation. Examples of vectors include plasmids, viruses and phages but any other vector that is commonly utilized in genetic engineering may be employed as well.

The invention further comprises a prokaryotic or eukaryotic host cell which is transformed or transfected with a vector of the invention. Prokaryotic cells such as *Escherichia coli* or *Bacillus subtilis*, or eukaryotic cells such as *Saccharomyces cerevisiae* are generally used for vector cloning and cDNA expression.

In addition, the hypoallergenic variants according to the invention can be produced as fusion proteins.

Thanks to their reduced IgE-reactivity, the Bet v 2 variants according to the present invention can be conveniently used for the preparation of pharmaceutical compositions (e.g. tablets) for the preventive or therapeutic treatment of individuals allergic to *Betula verrucosa* pollen.

In a further aspect the invention is therefore directed to a pharmaceutical composition containing an effective amount of hypoallergenic Bet v 2 variant as herein provided, optionally in combination with other allergens of *Betula verrucosa* and/or with pharmaceutically acceptable vehicles and excipients. In a preferred embodiment, the pharmaceutical composition is in the form of a vaccine to be used in the prophylaxis or therapy of allergic diseases, including bronchial asthma, allergic rhinitis, allergic dermatitis and allergic conjunctivitis. The theory and practice of vaccination are known to anyone skilled in the art (28, 29).

The following examples further illustrate the invention. Unless otherwise indicated, the methods used in the examples are described in Sambrook, Fritsch E T Maniatis "Molecular cloning. A laboratory manual" II ed. Vol. 1-2-3 CSH Lab Press 1989.

Figure 4:
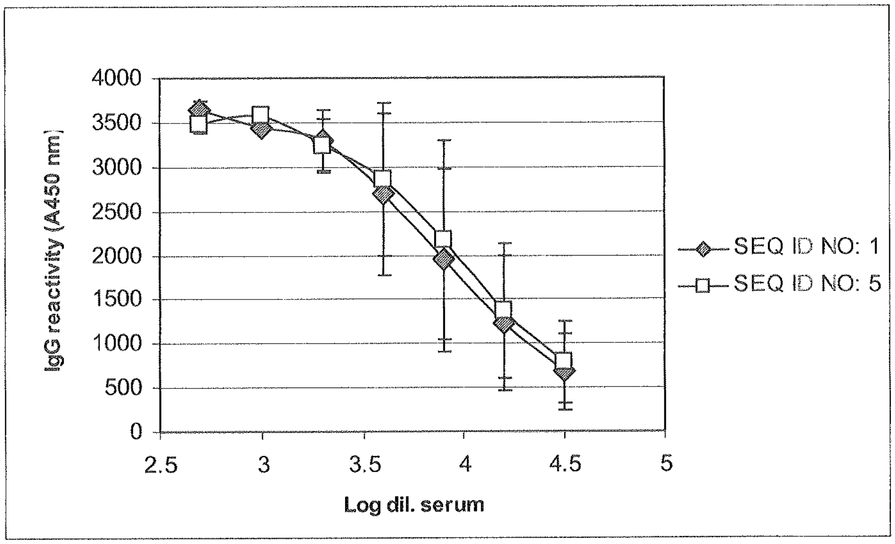

FIG. 1: ELISA analysis of IgE reactivity to Bet v 2 allergen and to Bet v 2 hypoallergenic variants;

FIG. 2: Inhibition of IgE binding to Bet v 2 allergen;

FIG. 3: Murine IgG response to respective immunogenic proteins;

FIG. 4: IgG response in mice immunized with SEQ ID NO:5.

EXAMPLE 1

Site-Specific Mutagenesis of the cDNA Coding for Bet v 2 Allergen

Site-specific mutagenesis of the cDNA coding for the Bet v 2 allergen (SEQ ID NO: 7) was carried out by cDNA cloning in a prokaryotic vector (pBluescript. GenBank acc. n. X52327) followed by PCR amplification. The oligonucleotides used as primers in the PCR reaction (Table) carried the appropriate base substitutions. For each mutagenesis, a complementary oligonucleotide binding to a corresponding region of the DNA strand was used (30). After amplification, the unaltered original template was selectively degraded with enzymatic digestion catalyzed by the restriction enzyme Dpnl. *Escherichia coli* cells were then transformed with the mutagenized molecules. Clones obtained from single bacterial colonies were sequenced according to Sanger to determine the correct base modification and the absence of non-specific mutations in the cDNA.

EXAMPLE 2

Production of Bet v 2 Protein and Variants Thereof

Wild-type (SEQ ID NO:7) and mutagenized (SEQ ID NOs: 8-12) Bet v 2 cDNAs, were cloned and expressed in *Escherichia coli* according to standard protocols (31, 32). The cells were collected by centrifugation, resuspended in a PBS 1× ($NaH_2PO_4$ 6.46 mM, $KH_2PO_4$ 1.47 mM, NaCl 136.89 mM) and lysed by sonication. The recombinant proteins were separated by centrifugation. The pellet containing an insoluble protein aggregate was resuspended in denaturing buffer PBS 1×, urea 6 M and stirred for 60 min at 4° C. The solubilized recombinant proteins were separated from insoluble debris by centrifugation, dialyzed against PBS 1×, filtered through a 1 μM filter and purified by affinity chromatography using agarose columns derivatized with poly-proline (Sigma, Milan, Italy). After washing with PBS 1×, urea 2 M, the recombinant proteins are eluted with PBS 1×, urea 8 M and refolded by dialysis for 16 hours at 4° C. in a PBS 1× solution.

EXAMPLE 3

Characteristics of Sera from Allergic Subjects

Sera were collected from individuals with clinical anamnesis of seasonal allergy to *Betula verrucosa* pollen and a RAST 3+ and 4+ specific reactivity to Bet v 2 allergen and then they were pooled and used in this form. A pool of sera from non-allergic patients was used as negative control.

EXAMPLE 4

ELISA Analysis of Bet v 2 Variants Reactivity to IgEs from a Serum Pool

The same quantity of wt allergen and of mutagenized variants (1 μg) in 50 mM carbonate/bicarbonate buffer, pH 9.6, were adsorbed on wells of polystirene plates for ELISA assay by incubation at 4° C. for 16 hours. The wells were washed with washing solution (60 mM phosphate buffer, pH 6.5, containing 0.05% Tween-20), and blocked with diluting solution (25% goat serum, 1 mM EDTA, 0.05% Tween 20, 0.01% Thiomersal in 150 mM phosphate buffer, pH 7.4). 70 μl aliquots in dilution buffer of a pool of human sera RAST 3+ and 4+ were added to each sample and incubated at 25° C. for 2 hours. After three washes, peroxidase-conjugated anti human-IgE serum (1:1500 in diluting buffer) was added, followed by incubation at 25° C. for 1.5 hours. After three washes, the colorimetric reaction was developed by adding 100 μl of TMB reagent (BioFX Laboratories, Owings Mills, Md.) and incubating for 15 minutes at 25° C. The reaction was stopped by adding 100 μl of 1 N HCl and read at 450 nm using a microplate reader spectrophotometer.

EXAMPLE 5

REAST Inhibition Assay, Bet v 2 Variants Inhibit the Binding Between Biotinylated Bet v 2 and the IgEs Contained in a Serum Pool Aliquots (50 μl) of a human serum pool RAST 4+ and 3+ to Bet v 2, diluted 1:3 in dilution buffer (25% goat serum, 1 mM EDTA, 0.05% Tween 20, 0.01% Thiomersal in 150 mM phosphate buffer, pH 7.4), were preincubated at 25° C. for 1.5 hrs with serial dilutions of wt allergen or mutants thereof, starting from 67 ng/ml. The mixtures were then added to ELISA polystirene plate wells adsorbed with human anti-IgE and incubated at 25° C. for 1.5 hrs. After three washes with phosphate buffer 0.06 M pH 6.5, Tween-20 0.05%, 0.1 ml of biotinylated But v 2 antigen were added (85.3 ng/ml) in dilution buffer at 25° C. for 1 hour. After three washes, peroxidase-streptavidin was added (0.1 μg/ml) for 30 min at 25° C. The colorimetric reaction was developed with 100 μl HCl 1N and spectrophotometrically read at 450 nm.

The percent inhibition was calculated as follows: 100×[(A−B)/A], where A is the absorbance measured at 450 nm in the absence of inhibitor and B is the absorbance in the presence of inhibitor.

EXAMPLE 6

Protocol for Immunization of Balb/c Mice

Two groups of 5 female Balb/c mice (Charles River) were subcutaneously immunized with 200 μl of an emulsion containing 100 μl complete Freund adjuvant and 20 μg antigen (SEQ ID NO:1, SEQ ID NO:5) in 100 μl saline. Three additional booster immunizations were carried out at 1-week intervals replacing the complete adjuvant with an incomplete one. As a control, five mice were administered a non-correlated antigen. Seven days after the last immunization, a blood sample was taken from the jugular vein and used in ELISA to control the antibody response against each immunogenic agent. In mice immunized with SEQ ID NO:5, the capability to recognize the wild-type protein was also analyzed.

EXAMPLE 7

ELISA Analysis of IgG-specific Response in Immunized Mice

The same quantities of wt Bet v 2 and of SEQ ID NO:5 variant (0.25 μg) in 50 mM carbonate/bicarbonate buffer, pH 9.6, were adsorbed on wells of polystyrene plates for ELISA assay by incubation for 16 hours at 4° C. The wells were washed with washing solution (60 mM phosphate buffer, pH 6.5, containing 0.05% Tween-20) and blocked with diluting solution (25% horse serum, 1 mM EDTA, 0.05% Tween 20, 0.01% Thiomersal in 150 mM phosphate buffer, pH 7.4). 100 μl aliquots of serial dilutions (in dilution buffer) of serum from each mouse were placed in the wells and incubated for 2 hours at 25° C.

After three washes, the peroxidase-conjugated anti mouse IgG serum was diluted 1:2000 in dilution buffer and added to the wells, followed by incubation for 1.5 hr at 25° C. After three washes, the colorimetric reaction was developed by adding 100 μl of TMB reagent (BioFX Laboratories, Owings Mills, Md.) and incubating for 15 min at 25° C. The reaction was stopped with 100 μl HCl 1 N followed by spectrophotometric reading at 450 nm. FIGS. 3 and 4 show the mean reactivity obtained by analysis of the sera from 5 mice for each group.

BIBLIOGRAPHY

1) Malling H. J., (1998) "Immunotherapy as an effective tool in allergy treatment". Allergy, 53: 461.
2) Toubi E., Kessel A., Blant A., Golan T. D., (1999) "Follow-up after systemic adverse reactions of immunotherapy". Allergy, 54(6): 617-620.
3) Akdis C. A., Blaser K., (2000) "Regulation of specific immune response by chemical and structural modifications of allergens". Int. Arch. Allergy Immunol., 121(4): 261-269.
4) Visco V, Dolecek C, Denépoux S, Le Mao J, Guret C, Rousset F, Guinnepain M T, Kraft D, Valenta R, Weyer A, Banchereau J, Lebecque S, (1996). "Human IgG monoclonal antibodies that modulate the binding of specific IgE to birch pollen Bet v 1". J. Immunol. 157: 956-962.
5) Vrtala S, Ball T, Spitzauer s, Pandjaitan B, Suphioglu C, Knox B, Sperr W R, Valent P, Kraft D, Valenta R. (1998). "Immunization with purified natural and recombinant allergens induces mouse IgG1 antibodies that recognize similar epitopes as human IgE and inhibit the human IgE-allergen interaction and allergen-induced basophil degranulation". J Immunol 160: 6137.
6) Breiteneder H., Pettenburger K., Bito A et al. (1989). "The gene coding for the major birch pollen allergen Bet v 1, is highly homologous to a pea disease resistance response gene". EMBO J, 8: 1935-1938.
7) Valenta R., Duchene M., Pettenburger K., Sillaber C., Valent P., Bettelheim P., Breitenbach M., Rumpold H., Kraft D., Scheiner O. (1991). "Identification of profilin as a novel pollen allergen; IgE autoreactivity in sensitized individuals.". Science 253:557-560
8) Goldschmidt-Clermont P J., Kim J., Machesky L M., Rhee S., Pollard T D. (1991). "Regulation of phospholipase C-γ by profilin and tytosine phosphorilation". Science, 251: 1231-3.
9) Carlsson I., Nystrom L E., Sundkvist F., Markey F., Lindberg U. (1977). "Actin polymerization is influenced by profilin, a low molecular weight protein in non muscle-cells". J Mol Biol, 115:465:83.
10) Mittermann I, Swoboda I, Pierson E, Eller N, Kraft D, Valenta R, Heberle-Bors E. (1995). "Molecular cloning and characterization of profilin from tobacco (*Nicotiana tabacum*): increased profilin expression during pollen maturation". Plant Mol Biol. 27(1):137-46.
11) Valenta R., Duchene M., Ebner C., Valent P., Sillaber C., Deviller P., Ferreira F., Tejkl M., Edelmann H., Kraft D., et al. (1992). "Profilins constitute a novel family of functional plant pan-allergens" J. Exp. Med, 175: 377-85.
12) Radauer C., Hoffmann-Sommergruber K. (2004). "Profilin". Plant food allergens. IN mills ENC, sherry PR, Editors. Plant food allergen. Oxford: Blackwell Pubishing. (2004). 105-24.
13) Niederberger V, Pauli G, Gronlund H, Froschl R, Rumpold H, Kraft D, Valenta R, Spitzauer S. (1998). "Recombinant birch pollen allergens (rBet v 1 and rBet v 2) contain most of the IgE epitopes present in birch, alder, hornbeam, hazel, and oak pollen: A quantitative IgE inhibition study with sera from different populations". J. Allergy Clin Immunol. 102:579-91.

14) Mari A., (2001). "Multiple pollen sensitization: a molecular approach to the diagnosis". Int Arch Allergy Immunol. 125: (57-65).

15) van Ree R., Voitenko V., van Leeuwen W A., Aalberse R C. (1992). "Profilin is a cross-reactive allergen in pollen and vegetabe foods". Int Arch Allergy Immunol 98:97:104.

16) Ganglberger E., Radauer C., Wagner S et al. (2001). "Hev b 8, the *Hevea brasiliensis* latex profilin, is a cross-reactive allergen of latex, plant foods and pollen". Int Arch Allergy Immunol. 125:216-27.

17) Giehl K Valenta R, Rothkegel M, Ronsiek M, Mannherz H G, Jockusch B M. (1994) "Interaction of plant profilin with mammalian actin". Eur J Biochem. 226(2):681-9.

18) Staiger C J, Yuan M, Valenta R, Shaw P J, Warn R M, Lloyd C W (1994). "Microinjected profilin affects cytoplasmic streaming in plant cells by rapidly depolymerizing actin microfilaments". Curr Biol. March 1; 4(3):215-9.

19) Rothkegel M, Mayboroda O, Rohde M, Wucherpfennig C, Valenta R, Jockusch B M. (1996). "Plant and animal profilins are functionally equivalent and stabilize microfilaments in living animal cells". J Cell Sci. 109 (Pt 1):83-90.

20) Almo S C, Pollard T D, Way M, Lattman E E (1994). "Purification, characterization and crystallization of Acanthamoeba profilin expressed in *Escherichia coli*". J Mol Biol. 236(3):950-2.

21) Fedorov A A, Pollard T D, Almo S C. (1994). "Purification, characterization and crystallization of human platelet profilin expressed in *Escherichia coli*". J Mol Biol. 241(3): 480-2.

22) Fedorov A A, Ball T, Mahoney N M, Valenta R, Almo S C. (1997). "The molecular basis for allergen cross-reactivity: crystal structure and IgE-epitope mapping of birch pollen profilin". Structure. 5: 33-45

23) Radauer C, Willerroider M, Fuchs H, Hoffmann-Sommergruber K, Thalhamer J, Ferreira F, Scheiner O, Breiteneder H. (2006). "Cross-reactive and species-specific immunoglobulin E epitopes of plant profilins: an experimental and structure-based analysis". Journal Clin Exp Allergy 2006; 36(7):920-929.

24) Rossi R E., Monasterolo G., Operti D., Corsi M. (1996). "Evaluation of recombinant allergens Bet v 1 and Bet v 2 (profilin) by Pharmacia CAP system in patients with pollen-related allergy to birch and apple". Allergy, 51:940-5.

25) Vrtala S, Wiedemann P, Mittermann I, Eichler H G, Sperr W R, Valent P, Kraft D, Valenta F. (1996). "High-level expression in *Escherichia coli* and purification of recombinant plant profilins: comparison of IgE-binding capacity and allergenic activity". Biochem Biophys Res Commun 226(1):42-50.

26) Wiedemann P, Giehl K, Almo S C, Fedorov A A, Girvin M, Steinberger P, Rudiger M, Ortner M, Sippl M, Dolecek C, Kraft D, Jockusch B, Valenta R. (1996). "Molecular and structural analysis of a continuous birch profilin epitope defined by a monoclonal antibody". J Biol Chem. 271(47): 29915-29921.

27) Lopez-Torrejon G, Diaz-Perales A, Rodriguez J, Sanchez-Monge R, Crespo J F, Salcedo G, Pacios L F. (2007). "An experimental and modeling-based approach to locate IgE epitopes of plant profilin allergens". J Allergy Clin Immunol. 119:1481-8.

28) Paul, (1989), "Fundamental Immunology", Raven press, New York.

29) Cryz, S. J. (1991), "Immunotherapy and Vaccines", VCH Verlagsgesellschaft.

30) Wang W., Malcolm B A. (2002). "Two-stage polymerase chain reaction protocol allowing introduction of multiple mutations, deletions, and insertions, using QuikChange site-directed mutagenesis". Methods Mol Biol. 182: 37-43.

31) Younghee Kim. (2004). "Cloning and Expression of a Lipase Gene from Rice (*Oryza sativa* cv. Dongjin)". Mol. Cells, 18(1): 40-45.

32) Asturias J A, Ibarrola I, Eseverri J L, Arilla M C, Gonzales-Rioja R, Martinez A. (2004). "PCR-based cloning and immunological characterization of *Parietaria judaica* pollen profilin". J Investig Allergol Clin Immunol, 14: 43-48.

The invention claimed is:

1. A hypoallergenic protein which is a sequence variant of the Bet v 2 major allergen and which is characterized by:

a) reduced reactivity to IgEs compared to wild-type Bet v 2 allergen (SEQ ID NO:1); and b) an amino acid sequence which consists of SEQ ID NO:1 with at least one substitution or deletion of the Ser or Lys residues matching $Ser_{39}$, $Lys_{45}$, $Lys_{88}$ or $Lys_{89}$ in SEQ ID NO:1.

2. A hypoallergenic protein according to claim 1, wherein said Ser or Lys residues are substituted with neutral, polar or acidic amino acids.

3. A hypoallergenic protein according to claim 2, wherein said neutral, polar or acidic amino acids are selected from Ala, Sly, Pro, Leu, Ile, Phe, Thr, Ser, Glu, Asp.

4. A hypoallergenic protein according to claim 3, wherein said amino acids are Ala, Thr, Ser, Gly, Glu, Asp.

5. A hypoallergenic protein according to claim 1, which is selected from the group consisting of SEQ ID NO: 2-6.

6. A peptide fragment of the hypoallergenic protein according to claim 1, wherein the peptide fragment consists of between 15 and 35 amino acids with at least one substitution and/or deletion of the Ser or Lys residues matching $Ser_{39}$, $Lys_{45}$, $Lys_{88}$ or $Lys_{89}$ in SEQ ID NO:1.

7. A pharmaceutical composition comprising an effective amount of a hypoallergenic protein according to claim 1, together with pharmaceutically acceptable vehicles and excipients.

8. A pharmaceutical composition comprising an effective amount of a peptide fragment according to claim 6, together with pharmaceutically acceptable vehicles and excipients.

* * * * *